United States Patent
Crutchfield et al.

(10) Patent No.: US 9,956,422 B2
(45) Date of Patent: May 1, 2018

(54) THERAPY DELIVERY METHODS AND CIRCUITS FOR AN IMPLANTABLE MEDICAL DEVICE

(71) Applicant: Medtronic, Inc., Minneapolis, MN (US)

(72) Inventors: Randolph E. Crutchfield, Scottsdale, AZ (US); Lonny V. Cabelka, San Clemente, CA (US); Mark R. Boone, Gilbert, AZ (US); Kevin P. Kuehn, Shoreview, MN (US); Marshall J. Rasmussen, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 491 days.

(21) Appl. No.: 14/260,309

(22) Filed: Apr. 24, 2014

(65) Prior Publication Data
US 2015/0306406 A1  Oct. 29, 2015

(51) Int. Cl.
| | |
|---|---|
| *A61N 1/39* | (2006.01) |
| *A61N 1/38* | (2006.01) |
| *A61N 1/362* | (2006.01) |
| *A61N 1/37* | (2006.01) |
| *A61N 1/05* | (2006.01) |

(52) U.S. Cl.
CPC ............ *A61N 1/385* (2013.01); *A61N 1/362* (2013.01); *A61N 1/3706* (2013.01); *A61N 1/3912* (2013.01); *A61N 1/3925* (2013.01); *A61N 1/3956* (2013.01); *A61N 1/3962* (2013.01); *A61N 1/3975* (2013.01); *A61N 1/0587* (2013.01)

(58) Field of Classification Search
CPC ............ A61N 1/36125; A61N 1/3912; A61N 1/3975; A61N 1/385
See application file for complete search history.

(56) References Cited

U.S. PATENT DOCUMENTS

| | | | |
|---|---|---|---|
| 4,949,720 A | 8/1990 | Thompson | |
| 5,201,865 A | 4/1993 | Kuehn | |
| 5,449,377 A | 9/1995 | Adams et al. | |
| 5,470,341 A * | 11/1995 | Kuehn | A61N 1/3931 607/14 |
| 5,527,346 A | 6/1996 | Kroll | |
| 5,755,742 A | 5/1998 | Schuelke et al. | |

(Continued)

OTHER PUBLICATIONS (PCT/US2015/027035) PCT Notification of Transmittal of the International Search Report and the Written Opinion of the International Searching Authority, dated Jul. 22, 2015, 9 pages.

*Primary Examiner* — Michael D Abreu

(57) ABSTRACT

Apparatus and methods for generating an induction waveform for performing threshold testing in an implantable medical device are disclosed. Such tests may be performed during the implant procedure, or during a device checkup procedure, or routinely during the lifetime of the device. The threshold test may include induction of an arrhythmia (such as ventricular fibrillation) followed by delivery of therapy at various progressively-increasing stimulation parameters to terminate the arrhythmia. As such, the capability to induce fibrillation within the device is desired. Induction of the arrhythmias may be accomplished via delivery of a relatively low energy shock or through delivery of an induction stimulation pulse to the cardiac tissue timed concurrently with the vulnerable period of the cardiac cycle.

9 Claims, 6 Drawing Sheets

(56) References Cited

U.S. PATENT DOCUMENTS

| | | |
|---|---|---|
| 5,899,929 A | 5/1999 | Thompson et al. |
| 6,016,445 A | 1/2000 | Baura |
| 6,175,765 B1 | 1/2001 | Sullivan et al. |
| 6,317,628 B1 | 11/2001 | Linder et al. |
| 6,620,186 B2 | 9/2003 | Saphon et al. |
| 6,931,279 B2 | 8/2005 | Ousdigian et al. |
| 6,963,773 B2 | 11/2005 | Waltman et al. |
| 7,555,338 B2 | 6/2009 | Ostroff |
| 7,877,139 B2 | 1/2011 | Ostroff |
| 8,064,996 B2 | 11/2011 | Belk et al. |
| 8,340,762 B2 | 12/2012 | Vonk et al. |
| 8,423,136 B2 | 4/2013 | Ostoff |
| 8,452,399 B2 | 5/2013 | Wanasek |
| 2006/0241698 A1* | 10/2006 | Ostroff .................. A61N 1/385 607/2 |
| 2007/0270911 A1 | 11/2007 | Doerr et al. |
| 2010/0324618 A1 | 12/2010 | Wanasek |
| 2012/0116483 A1 | 5/2012 | Yonezawa et al. |
| 2012/0197325 A1* | 8/2012 | Sauer .................. A61N 1/3981 607/5 |
| 2013/0035735 A1 | 2/2013 | Kroll |
| 2013/0241628 A1* | 9/2013 | Zhang .................. H03K 17/16 327/439 |

\* cited by examiner

THERAPY DELIVERY METHODS AND CIRCUITS FOR AN IMPLANTABLE MEDICAL DEVICE

FIELD

The present invention relates generally to implantable medical devices. In particular, the disclosure relates to methods, components, and circuits for therapy delivery by the implantable medical devices.

BACKGROUND

The human anatomy includes many types of tissues that can either voluntarily or involuntarily, perform certain functions. After disease, injury, or natural defects, certain tissues may no longer operate within general anatomical norms. For example, organs such as the heart may begin to experience certain failures or deficiencies. Some of these failures or deficiencies can be diagnosed, corrected or treated with an implantable medical device (IMD). For example, an implanted IMD may detect an arrhythmia, such as ventricular fibrillation, and deliver one or more electrical pulses to stop the arrhythmia and allow the heart to reestablish a normal sinus rhythm.

Examples of such IMDs include subcutaneous implantable cardioverter/defibrillator (SICD) systems that provide synchronous cardioversion shocks and/or asynchronous defibrillation shocks and subcutaneous pacemaker/cardioverter/defibrillator (SPCD) systems that provide additional staged therapies of anti-tachyarrhythmia pacing, synchronous cardioversion shocks and asynchronous defibrillation shocks. In general, the IMDs deliver a first pulse at a first energy level upon detecting an arrhythmia and, if the arrhythmia is not stopped, deliver additional pulses at increasing energy levels until the arrhythmia is stopped or the programmed progression of pulses has been exhausted.

Typically, threshold testing is performed to evaluate the effectiveness of an IMD in ending episodes of arrhythmia. For example, the energy levels or waveforms of pulses delivered by the IMD, the sensitivity of the IMD to detect ventricular fibrillation, or the position of the electrodes used to deliver the pulses, can be configured as necessary to assure the effectiveness of the IMD. The threshold testing may be performed during the implantation process, during subsequent follow-up sessions and/or during the automatic configuration sessions initiated by the IMD. One method of testing an IMD's capability to reliably defibrillate the heart involves induction of an episode of an arrhythmia in the patient's heart, and then allowing the IMD to detect and terminate the induced arrhythmia. The IMD itself has the capability of inducing arrhythmia during the threshold testing procedures.

The IMD induces an arrhythmia by delivering a pulse during the period of vulnerability within a cardiac cycle, e.g., during or near the T-wave, delivering a high frequency pulse train, delivering direct current, or other known methods for inducing the fibrillation. The clinician may program the stimulation parameters for the induction attempt, such as the timing, amplitude, or other characteristics of a T-wave shock. If the induction attempt fails, the new stimulation parameters are used for another induction attempt.

When an induction attempt succeeds, the IMD can fail to detect the arrhythmia, or fail to stop the arrhythmia. In such cases, the detection algorithm or the pulse progression must be modified. The process repeats until successful arrhythmia induction, detection, and defibrillation occur such that the effectiveness of the IMD is confirmed.

The process of confirming the effectiveness of an IMD can be time and resource consuming both for the clinician and for the IMD. For example, a clinician programs the IMD to execute an initial arrhythmia detection algorithm, and programs an initial progression of pulses to be delivered in response to a detected arrhythmia. The clinician then programs the IMD to induce the heart to fibrillate, so that the programmed detection algorithm and pulse progression can be tested. During automatic configuration sessions, the device may also consume a large amount of the internally stored energy to perform those functions. Accordingly, there remains a need for improved circuits and methods for therapy delivery.

SUMMARY

It is desired to perform threshold testing to evaluate the efficacy of the therapy delivered by a subcutaneous or substernal implantable medical device (SIMD). The threshold testing may be performed during the implant procedure, or during an IMD checkup procedure, or during automatic configurations of the IMD over the lifetime of the device.

In accordance with embodiments of the present disclosure, the SIMD includes circuits for generating and delivering therapy and arrhythmia induction stimulation pulses. The circuits include an output circuit having a plurality of switches that are arrayed in the shape of a "H" to form a H-bridge circuit. In some embodiments, the output circuit further includes at least one opt-in circuit that is coupled in parallel to one of the switches. The output circuit is configured such that the opt-in circuit is utilized to bypass the switch element of the H-bridge during delivery of arrhythmia induction stimulation pulses.

Exemplary methods for the threshold testing may include induction of an arrhythmia (such as ventricular fibrillation) followed by delivery of therapy at various progressively increasing stimulation parameters to terminate the arrhythmia. The induction of the arrhythmias may be accomplished via delivery of a relatively low energy induction stimulation pulse or through delivery of two or more induction stimulation pulses to the cardiac tissue timed concurrently with the vulnerable period of the cardiac cycle.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

Currently, implantable medical devices (IMD), such as the implantable cardioverter/defibrillator (ICD), use endocardial or epicardial leads which extend from the ICD housing through the venous system to the heart. Electrodes positioned by the leads in or adjacent to the heart are used for therapy delivery and sensing functions. Cardioversion and defibrillation shocks are generally applied between a coil electrode carried by one of the leads and the ICD housing, which acts as an active can electrode. A subcutaneous or substernal implantable medical device (SIMD) differs from the more commonly used IMD in that the housing and leads are typically implanted subcutaneously such that the sensing and therapy are accomplished subcutaneously. The SIMD does not require leads to be placed in or on the cardiac tissue. Instead, the SIMD makes use of one or more electrodes on the housing, together with one or more leads that carry one or more electrodes for therapy delivery and/or sensing, which are implanted in the subcutaneous or substernal space.

The disclosure describes techniques, components, devices, and methods for performing threshold testing of an SIMD. In this disclosure, the stimulation pulses that are delivered for the threshold testing will be referred to as arrhythmia induction stimulation pulses (or simply as induction stimulation pulses).

In this disclosure, "substernal space" refers to the region defined by the undersurface between the sternum and the body cavity but not including the pericardium. In other words, the region is dorsal to the sternum and ventral to the ascending aorta. The substernal space may alternatively be referred to by the terms "retrosternal space" or "mediastinum" or "infrasternal" as is known to those skilled in the art and includes the region referred to as the anterior mediastinum. For ease of description, the term substernal space will be used in this disclosure, it being understood that the term is interchangeable with any of the other aforementioned terms.

In this disclosure, the term "extra-pericardial" space refers to the region around, but not in contact with, the outer heart surface. The region defined as the extra-pericardial space includes the gap, tissue, bone, or other anatomical features around the perimeter of, and adjacent to, but not in contact with the pericardium.

In this disclosure therapy stimulus pulse information such as stimulus amplitude, duration, rate, and/or waveform type (e.g., mono-phasic, bi-phasic, tri-phasic, or multi-phasic, etc.) and the like are included under the rubric of "stimulation parameters."

Figure 1:
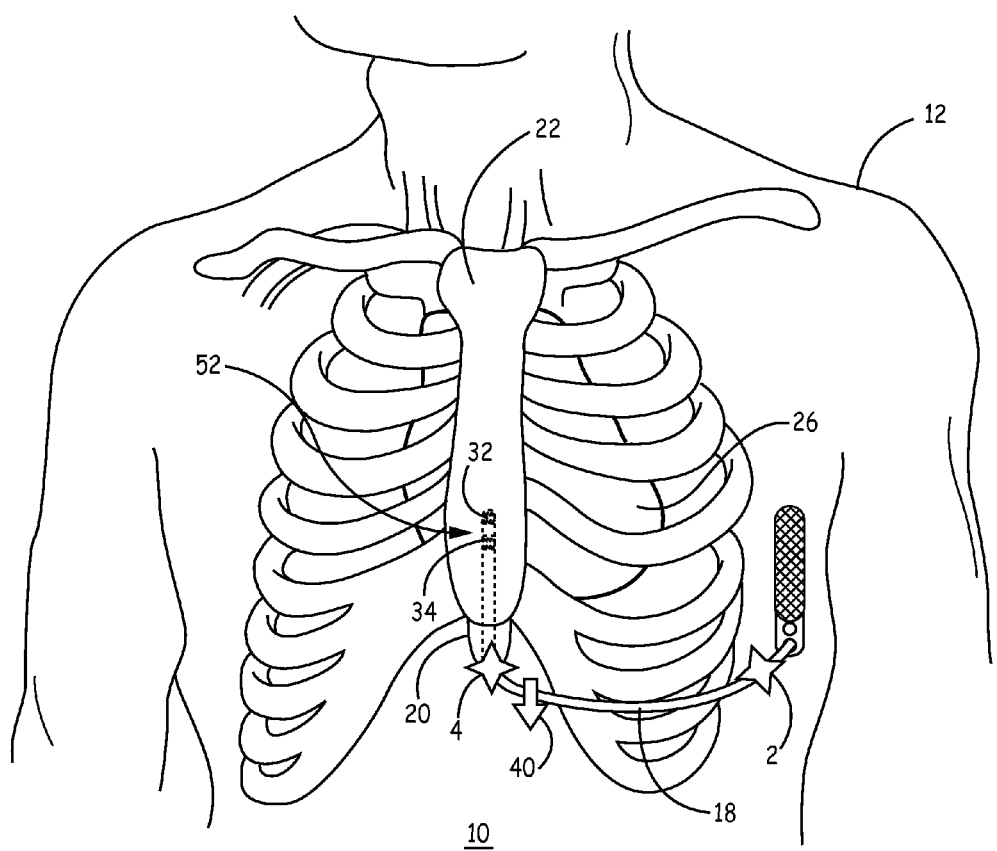
FIG. 1 is a front view of a patient implanted with an implantable cardiac system.
Figure 2:
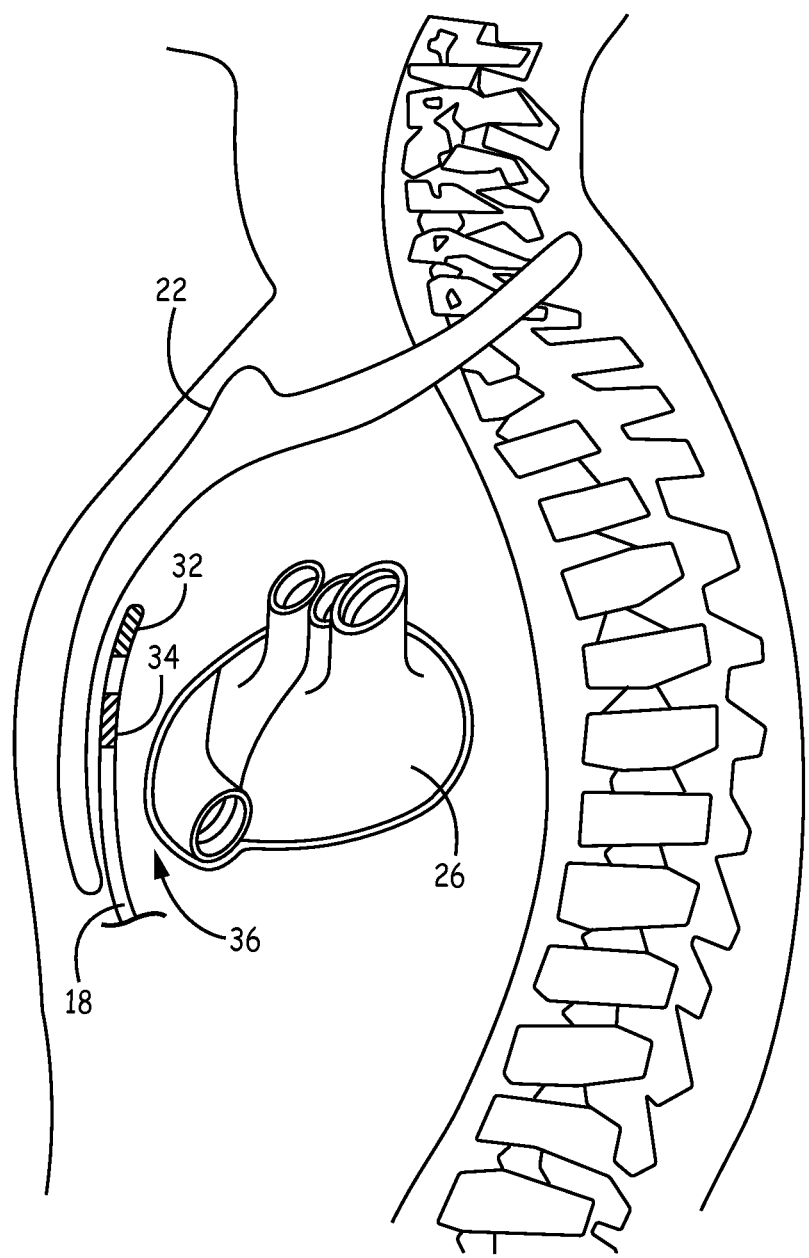
FIG. 2 is a side view of the patient implanted with the implantable cardiac system.

FIGS. 1-2 are conceptual diagrams of a patient 12 implanted with an exemplary implantable cardiac system 10. FIG. 1 is a front view of patient 12 implanted with implantable cardiac system 10. FIG. 2 is a side view patient 12 with implantable cardiac system 10.

Implantable cardiac system 10 includes a subcutaneous/substernal implantable medical device (SIMD) 14 connected to a lead 18. The lead 18 may be utilized for sensing and/or to provide an electrical stimulation pulse such as pacing or defibrillation. Lead 18 includes electrodes 32 and 34 that may be configured for delivery of the stimulation pulse. In addition, or alternatively, the electrodes 32, 34 may be configured for sensing.

SIMD 14 may provide stimulation pulse therapy and/or sense electrical activity of heart 26 via a combination of delivery/sensing vectors that include combinations of electrodes 32 and 34 and the housing or can electrode of SIMD 14. For example, SIMD 14 may deliver therapy or obtain electrical signals sensed using a delivery/sensing vector between electrodes 32 and 34, or using a delivery/sensing vector between electrode 32 and the conductive housing or can electrode of SIMD 14, or using a delivery/sensing vector between electrode 34 and the conductive housing or can electrode of SIMD 14, or a combination thereof. In this manner, sensing and stimulation pulses including defibrillation therapy, ATP therapy or post shock pacing (or other pacing therapy) may be provided in an ICD system without entering the vasculature or the pericardial space, nor making intimate contact with the heart.

The electrodes 32 and 34 may be located near a distal end of lead 18. Electrodes 32 and 34 may comprise ring electrodes, hemispherical electrodes, coil electrodes, helix electrodes, or other types of electrodes, or combination thereof. Electrodes 32 and 34 may be the same type of electrodes or different types of electrodes.

The lead body of lead 18 also includes one or more elongated electrical conductors (not illustrated) that extend through the lead body from the connector assembly of SIMD 14 provided at a proximal lead end to electrodes 32, 34. The lead body of lead 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of leads 16 and 18 may engage with respective ones of electrodes 32, 34. The respective conductors may electrically couple to circuitry, such as a therapy module or a sensing module, of SIMD 14 via connections in connector assembly, including associated feedthroughs. The electrical conductors transmit therapy from a therapy module within SIMD 14 to one or more of electrodes 32, 34 and transmit sensed electrical signals from one or more of electrodes 32, 34 to the sensing module within SIMD 14.

In the example illustrated in FIGS. 1-2, SIMD 14 is implanted subcutaneously on the left midaxillary of patient 12. SIMD 14 may, however, be implanted at other subcutaneous locations on patient 12. The lead 18 may be inserted through an incision 2 or 4 on the patient's body for subcutaneous and/or extrapericardial implantation as will be described in more detail below.

Lead 18 includes a proximal end that is connected to SIMD 14 and a distal end that includes one or more electrodes. Lead 18 may be implanted within the mediastinum such that one or more electrodes 32 and 34 are located over a cardiac silhouette of the ventricle as observed via fluoroscopy. In the example illustrated in FIGS. 1-2, lead 18 is located substantially centered under sternum 22. Lead 18 extends subcutaneously from SIMD 14 toward xiphoid process 20. At a location near xiphoid process 20 lead 18 bends or turns and extends superior upward in the substernal space. In one example, lead 18 may be placed in the mediastinum 36 and, more particularly, in the anterior mediastinum. The anterior mediastinum is bounded laterally by pleurae, posteriorly by pericardium, and anteriorly by sternum 22. In other instances, however, lead 18 may be implanted such that it is offset laterally from the center of sternum 22. Alternatively, lead 18 may be placed such that a therapy vector between one of electrodes 32,34 and a housing or can electrode of SIMD 14 is substantially across the ventricle of heart 26. Although described herein as being implanted in the substernal space, the mediastinum, or the anterior mediastinum, lead 18 may be implanted in other extra-pericardial locations.

The configuration described above in FIGS. 1-2 is directed to providing ventricular pacing via lead 18. In situations in which atrial pacing is desired in addition to or instead of ventricular pacing, lead 18 may be positioned further superior. A pacing lead configured to deliver pacing pulses to both the atrium and ventricle may have more electrodes. For example, the pacing lead may have one or more electrodes located over a cardiac silhouette of the atrium as observed via fluoroscopy and one or more electrodes located over a cardiac silhouette of the ventricle as observed via fluoroscopy. In some instances, two substernal pacing leads may be utilized with one being an atrial pacing lead implanted such that the electrodes are located over a cardiac silhouette of the atrium as observed via fluoroscopy and the other being a ventricle pacing lead being implanted such that the electrodes are located over a cardiac silhouette of the ventricle as observed via fluoroscopy.

SIMD 14 may include a housing that forms a hermetic seal that protects components of SIMD 14. The housing of SIMD 14 may be formed of a conductive material, such as titanium. SIMD 14 may also include a connector assembly (also referred to as a connector block or header) that includes electrical feedthroughs through which electrical connections are made between conductors within lead 18 and electronic components included within the housing. Housing may enclose one or more processors, memories, transmitters, receivers, sensors, sensing circuitry, therapy circuitry and other appropriate components as is known in the art. SIMD 14 is configured to be implanted in a patient, such as patient 12.

As shown in FIG. 1, an anchoring mechanism 40 may be provided along the lead body to couple the lead 18 at an access point 4 through which the distal end of the lead 18 is inserted into the substernal space. The access point 4 is any location that provides access into the substernal space. In one exemplary embodiment, the access point 4 is adjacent to or below the xiphoid process (also referred to as "subxiphoid"). The access point may also be at the notch (not shown) that connects the xiphoid process to the sternum. In other embodiments, the substernal space may also be accessed through the manubrium. The anchoring mechanism 40 is fixedly-coupled to cartilage, musculature, tissue or bone at the entry point into the substernal space at or near the access point at which site the body of the lead 18 transitions from the subcutaneous tissue into the substernal space of patient 12.

The examples illustrated in FIGS. 1-2 are exemplary in nature and should not be considered limiting of the techniques described in this disclosure. In other examples, SIMD 14 and lead 18 may be implanted at other locations. For example, SIMD 14 may be implanted in a subcutaneous pocket in the right chest. In this example, lead 18 may be extend subcutaneously from the device toward the manubrium of the sternum and bend or turn and extend subcutaneously inferiorly from the manubrium of the sternum, substantially parallel with the sternum.

In addition, it should be noted that system 10 may not be limited to treatment of a human patient. In alternative examples, system 10 may be implemented in non-human patients, e.g., primates, canines, equines, pigs, and felines. These other animals may undergo clinical or research therapies that may benefit from the subject matter of this disclosure.

Figure 3:
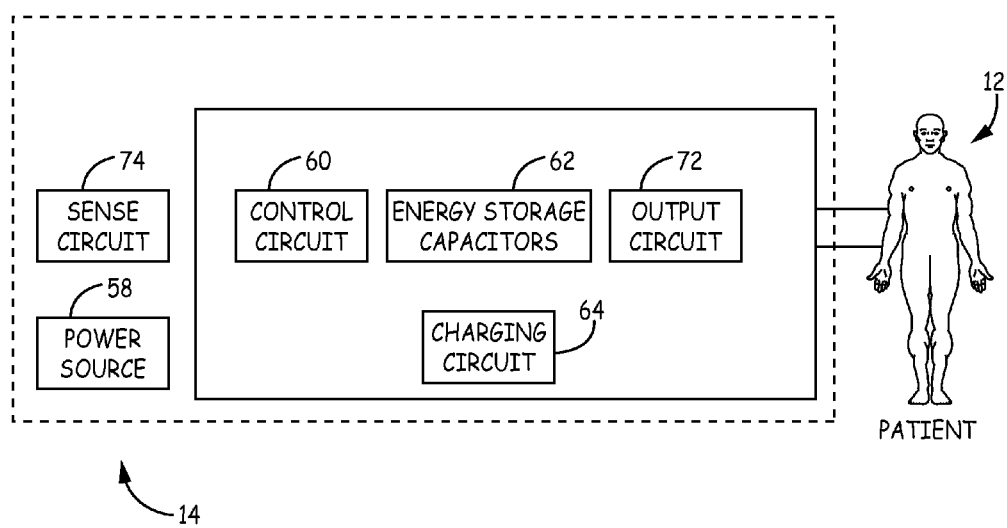
FIG. 3 is a block diagram of a subcutaneous/substernal SIMD of the implantable cardiac system.

FIG. 3 is a block diagram of SIMD 14 that is connected to a patient 12. The SIMD 14 includes a control circuit 60 that is connected to at least two energy storage capacitors 62a, and 62b (collectively "62") via a charging circuit 64. During the operation of the SIMD 14, the control circuit 60 controls various functions of the SIMD 14 such as stimulation pulse delivery or sensing. For example, the control circuit 60 controls the delivery of stimulation pulses for threshold testing to maximize the efficiency of the therapy delivered based on a selected one or more therapy programs, which may be stored in memory. Among other things, the control circuit 60 issues signals to regulate the charging circuit 64 to charge the energy storage capacitors 62 to a desired voltage level. Feedback on the voltage level of the energy storage capacitors 62 is provided to the control circuit 60. A power source 58 is provided in SIMD 14 and may be coupled to charging circuit 64 to provide the energy that is utilized to generate the stimulation pulses.

The control circuit 60 may include any type of circuitry that can issue control signals for controlling the various functions of SIMD 14. For example, the control circuit 60 is generally representative of a processor and associated memory. The memory, for example, may include computer readable instructions that, when executed by processor, cause the components of the SIMD 14 to perform various functions attributed to them. For example, the memory may include any non-transitory, computer-readable storage media including any combination of one or more of a volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

To facilitate therapy delivery, the SIMD 14 may deliver the therapy in response to sensed physiological conditions. As such, SIMD 14 may include sense circuitry 74 that is coupled to the control circuit 60. For example, sense circuitry 74 may include one or more sense amplifier circuits receiving cardiac signals to monitor the heart (e.g., sense evoked responses of the heart), such as described, for example, in U.S. Pat. No. 5,861,013, to Peck et al., or, for example, in U.S. Pat. No. 5,117,824, to Keimel et al., entitled Apparatus for Monitoring Electrical Physiologic Signals," both of which are incorporated herein by reference in their entirety.

The functions attributed to SIMD 14 herein may be embodied as one or more processors, hardware, firmware, software, or any combination thereof. Depiction of different features as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components. For example, sensing circuitry 74 for receiving and converting analog electrical signals received from other SIMD modules or sensors may be implemented in hardware and software included in control circuit 60.

After charging to a desired level, the energy stored in the energy storage capacitors 62 may be delivered to the patient 12 in the form of stimulation pulses. Control circuit 60 may be connected to the output circuit 72 to control the delivery of the stimulation pulses. The application of appropriate control signals causes the output circuit 72 to deliver the energy received from the capacitors 62 in the form of stimulation pulses. The energy is delivered to the patient 12 attached to the SIMD 14 over a set of electrodes that may be selected from one or more of the electrodes on the lead(s) (e.g., 32, 34), and/or the can/housing electrode. The control circuit 60 may verify the integrity of the output circuit 72 before and during the transfer of the stimulation pulse. In accordance with aspects of the present application, some of the components of SIMD 14 are disclosed in FIGS. 4-5.

To avoid unnecessarily obscuring the inventive aspects of the disclosure, it should be understood that numerous other components of SIMD 14 have not been shown. Examples of such additional components and/or circuit configurations for the operational circuitry employed in SIMD 14 can take any of the known forms that detect a tachyarrhythmia from the sensed ECG and provide cardioversion/defibrillation shocks as well as post-shock pacing as needed while the heart recovers. Such components include circuitry for powering and controlling various sensing and therapy delivery functions. An exemplary simplified block diagram of such circuitry adapted to function employing the sensing and therapy delivery electrodes described herein is set forth in U.S. Pat. No. 7,647,095, "Method and Apparatus for Verifying a Determined Cardiac Event in a Medical Device Based on Detected Variation in Hemodynamic Status" to Bhunia and in U.S. Pat. No. 8,155,740, "Constant Current Pacing Apparatus and Pacing Method" to Wanasek, which are both incorporated herein by reference in their entirety. It will be understood that the simplified block diagram does not show all of the conventional components and circuitry of such devices including digital clocks and clock lines, low voltage power supply and supply lines for powering the circuits and providing pacing pulses or telemetry circuits for telemetry transmissions between the SIMD 14 and an external programmer.

Figure 4:
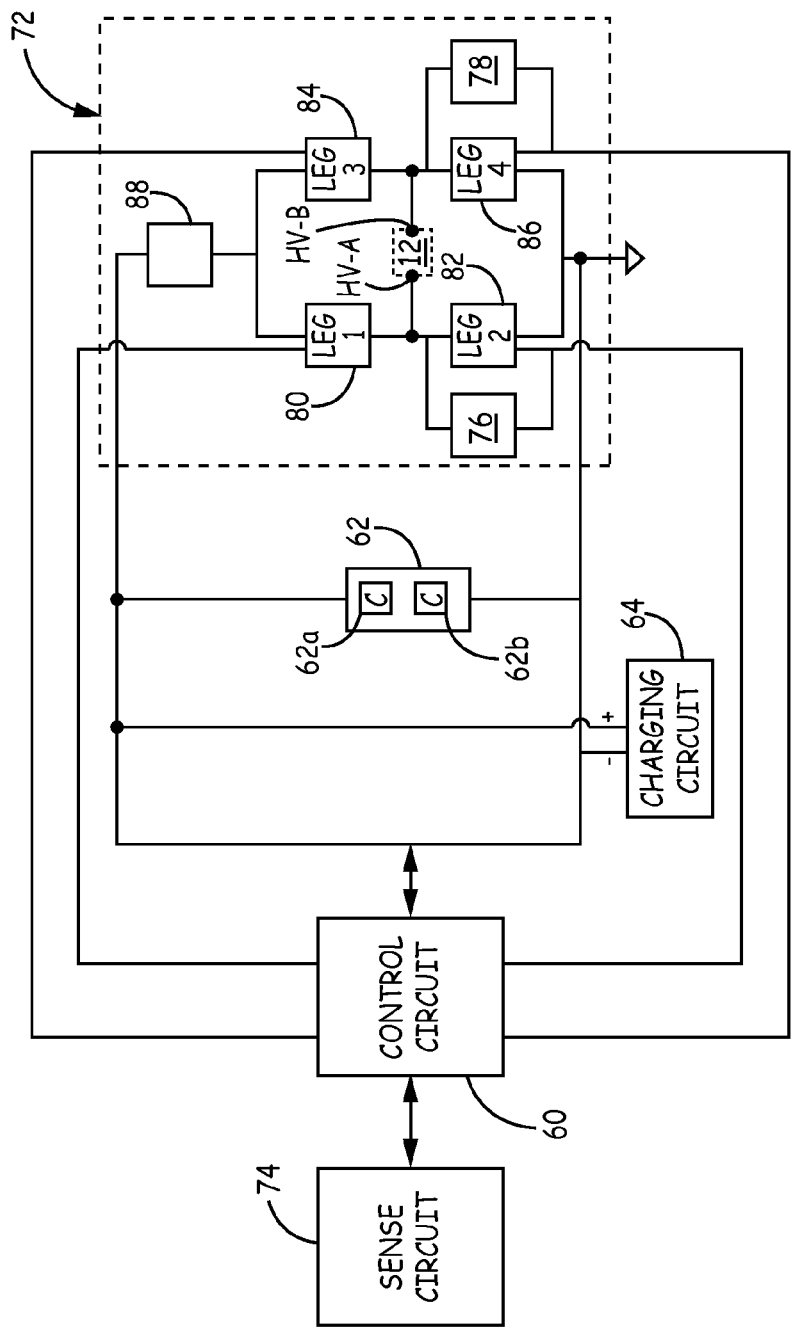
FIG. 4 illustrates an exemplary schematic showing a portion of the operational circuitry of the SIMD in accordance with an embodiment of the disclosure.

FIG. 4 illustrates an exemplary schematic showing a portion of the operational circuitry of SIMD 14 in accordance with an embodiment of the disclosure. The output circuit 72 allows the controlled delivery of energy from the energy storage capacitors 62 to the patient 12. The energy may be delivered to provide one or more functions of the SIMD 14 such as therapy delivery, or threshold testing for pacing or defibrillation therapies. Collectively, the energy delivered for various therapies (such as pacing, defibrillation) and threshold testing is performed in accordance with a treatment regimen that may be pre-programmed into SIMD 14 (such as the aforementioned processor/memory) and updated during the operational life of the SIMD 14, as is known in the art.

The output circuit 72 includes four switches 80, 82, 84, and 86 that are interconnected. As is shown in FIG. 4, the switches 80, 82, 84, and 86 are arrayed to define a configuration that is commonly referred to as a "H-bridge". In other words, the four interconnected switches are arrayed having switches 80 and 84 that are connected to the high side and switches 82 and 86 that are connected to the low side.

Output circuit 72 further includes opt-in circuit 76 and opt-in circuit 78 that are electrically coupled to the switches 80-86. In one embodiment, the opt-in circuit 76 is connected in parallel with switch 82 such that a first end is connected at an intersection point of the interconnected terminals for switches 80 and 82 and a second end is connected to the other terminal of switch 82. The opt-in circuit 78 is connected in parallel with switch 86 such that a first end is connected at an intersection point of the interconnected terminals for switches 84 and 86 and a second end is connected to the other terminal of switch 86. As will be described in more detail below, the opt-in circuits 76, 78 include conducting devices that when configured in accordance with predetermined criteria will cause a stimulation pulse to bypass the switches 82 and 86 during one or more operations of the SIMD 14.

As shown in FIG. 4, the intersection of the switches 80-86 includes HV-A and HV-B terminals that couple the output circuit 72 to the therapy delivery and sense electrodes. The SIMD 14 delivers stimulation pulses to patient 12 typically through at least two electrodes (e.g., via one or more of electrodes 32, 34 (FIGS. 1, 2), and/or the can electrode) that are coupled to terminal HV-A and terminal HV-B according to predetermined therapy or other treatment regimens.

Switches 80 and 84 are coupled through a discharge switch 88 to a positive terminal of the energy storage capacitors 62. Discharge switch 88 is controlled by control circuit 60 to be biased in a conducting (closed) state and remain in the conducting state during discharge of the capacitors 62. Switches 82 and 86 are coupled to a negative terminal of the energy storage capacitors 62. The selection of one or more of the switches 80, 82, 84, and 86 under control of control circuit 60 may be used to provide one or more functions. For example, selection of certain switches in one or more configurations may be used to provide one or more types of stimulation pulses such as pacing, cardioversion, or defibrillation, or may be used for threshold testing, or may be used to remove DC polarization of the tissue-to-electrode interface, etc.

In accordance with aspects of this disclosure, the switches 80, 82, 84, 86 are biased into one of a conducting or non-conducting state to deliver one or more stimulation pulses to effect various predetermined operations of the SIMD 14. The switches 80-86 may be implemented as power semiconductor devices that may be operated as an electronic switch. Examples of power semiconductor devices include thyristors, silicon controlled rectifiers (SCRs), insulated-gate bipolar transistors (IGBTs), metal oxide semiconductor field effect transistors (MOSFETs such as N-channel or P-Channel MOSFETs, BiMOSFETs), either employed alone or in electrical series with high voltage thyristers or "triacs" or having a current blocking component such as a diode connected across the source and drain, a body diode, etc, associated therewith. The discharge switch 88 may be implemented as a power semiconductor device operated as an electronic switch (including for example an IGBT, or a BiMOSFET, or any of the other devices disclosed herein). As is known in the art, such semiconductor devices may be switched into conduction based on signals that are issued by control circuit 60 alone, or by dedicated drive circuits which respond to low voltage control signals, or a combination of both.

Control circuit 60 issues control signals that cause the output circuit 72 to be configured in one of a plurality of configurations each of which is selected to provide one or more functions of the SIMD 14. For example, in accordance with an embodiment, the SIMD 14 provides a biphasic therapy stimulation pulse to the patient in the following manner. With reference to FIG. 4, the opt-in circuits 76 and 78 are biased in a non-conducting (open) state during delivery of the therapy stimulation pulse. Once the energy storage capacitors 62 are charged to a selected energy level, the switches 80, 86, and 82 are biased in a conducting state in order to provide a path from the capacitors 62 to electrodes (e.g., 32, 34) for the application of a first phase of a therapy stimulation pulse to the patient 12. The stored energy discharged by capacitors 62 is conducted from the positive terminal of the capacitors, through switch 80, across the patient 12, back through switch 86 to the negative terminal of the capacitors 62. The first phase of the biphasic pulse therefore applies a positive pulse from the electrode 32 to the electrode 34.

Before the energy storage capacitors 62 are completely discharged, switches 80 and 86 are biased in a non-conducting state in preparation for application of the second phase of the biphasic pulse. For example, biasing the switches 80-86 in a non-conducting state may be achieved by opening switch 88 to shut off the current flow in accordance with one embodiment. In other embodiments, the control circuit 60 may issue signals to control the biasing of each of the switches.

After the end of the first phase of the biphasic therapy stimulation pulse, the switches 88, 84 and 82 are biased in a conducting state to start the second phase of the biphasic pulse. Switches 84 and 82 provide a path to apply a negative therapy stimulation pulse to the patient 12. With reference to FIG. 4, the energy travels from the positive terminal of the capacitors 62, through switch 84, across the electrodes 34, 32 coupled to the patient 12, and out through switch 82 to the negative terminal of the capacitors 62. The polarity of the second phase of the therapy stimulation pulse is therefore opposite in polarity to the first phase of the pulse.

In another example, the SIMD 14 will perform threshold testing to determine optimum stimulation parameters for therapy delivery. SIMD 14 induces fibrillation of heart 12, e.g., ventricular fibrillation, to test the effectiveness of the SIMD 14 in detecting and stopping the fibrillation. SIMD 14 induces fibrillation according to a fibrillation induction protocol included in the patient's treatment regimen, and is capable of employing a plurality of fibrillation protocols to induce fibrillation. Exemplary fibrillation induction protocols include delivery of an electrical pulse to heart 12 during the T-wave of a cardiac cycle, delivery of a high-frequency pulse train, and delivery of direct current. The disclosure is not limited to the exemplary induction protocols, and SIMD 14 can induce fibrillation according to any of a number of fibrillation induction protocols known in the art. SIMD 14 detects fibrillation employing one or more fibrillation detection techniques known in the art. SIMD 14 can be programmed to deliver a progression of therapies, e.g., pulses with increasing energy levels, until the detected fibrillation of heart 12 is stopped.

Accordingly, techniques of the present invention utilize the output circuit 72 in a predetermined arrangement to deliver the stimulation pulse(s) for the therapy delivery (such as an induction stimulation pulse) in accordance with the patient's treatment regimen. In response to charging the energy storage capacitors 62 to a selected energy level, the opt-in circuit 78 and switches 80, 88 are biased in a conducting state in order to provide a path from the capacitors 62 to electrodes 32, 34 for the application of a first phase of a stimulation pulse to the patient 12. Biasing of the opt-in circuit 78 will be described in more detail below. The stored energy travels from the positive terminal of the capacitors, through switch 80, across the patient 12, back through opt-in circuit 78 to the negative terminal of the capacitors 62. Switches 82, 84, and 86 are biased in a non-conducting state during the first phase. As such, the lower half of the H-bridge is bypassed in this first phase.

After the end of the first phase of the stimulation pulse delivery, the opt-in circuit 76 and switches 88, 84 are biased in a conducting state for the second phase of the biphasic stimulation pulse. Biasing of the opt-in circuit 76 will be described in more detail below. Switch 84 and the opt-in circuit 76 provide a path to apply a negative stimulation pulse to the patient 12. With reference to FIG. 4, the energy travels from the positive terminal of the capacitors 62, through switch 84, across the electrodes 34, 32 coupled to the patient 12 and back through opt-in circuit 76 to the negative terminal of the capacitors 62. The polarity of the second phase of the stimulation pulse is therefore opposite in polarity to the stimulation pulse delivered in the first phase.

Figure 5:
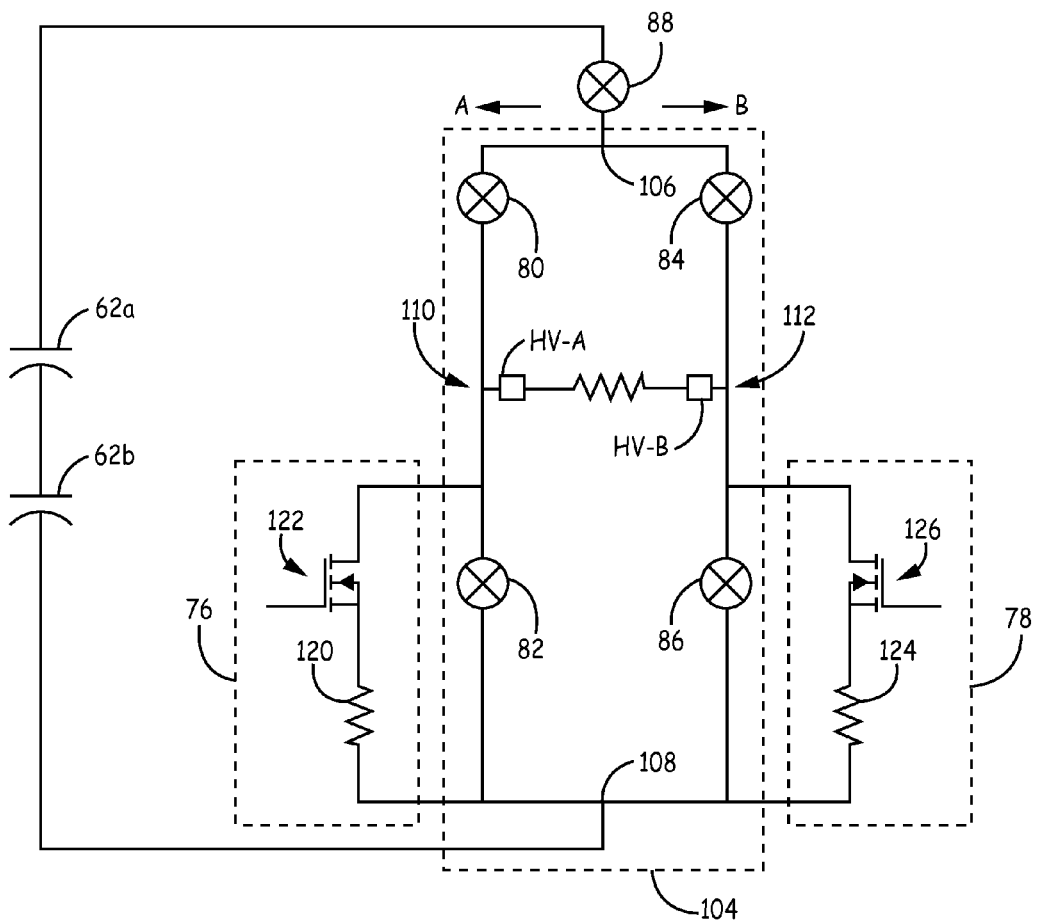
FIG. 5 shows an exemplary schematic diagram of the output circuit, such as functionally shown in FIG. 4.

Exemplary embodiments of the output circuit 72 of FIG. 4 are shown in FIG. 5. As described in reference to FIG. 4, the four output switches 80, 82, 84, and 86 allow the transfer of energy from the energy storage capacitors 62. Switches 80-84 may be implemented as any of the power semiconductor devices mentioned above. In such an embodiment, the semiconductor devices may be controlled by the control circuit 60 from a conducting to a non-conducting state. The four output switches 80, 82, 84, and 86 can be switched from a non-conducting to a conducting condition based on control signals provided by the control circuit 60.

FIG. 5 shows an exemplary schematic diagram of an output circuit 72, such as functionally shown in FIG. 4. Table 1, below, shows the operation of the output circuit 72 of FIG. 5 to provide various functions of SIMD 14, with A and B representing the direction of current flow during a given function. Table 1 shows the biasing of the switches 76-88 of the output circuit 72 during delivery of therapy stimulation pulses denoted by the references "A-B Delivery," "B-A Delivery," "A-B Post Shock Pace," "B-A Post Shock Pace" and the induction stimulation pulse denoted by the references "A-B Induction," and "B-A Induction".

TABLE 1

| Switch | A-B Delivery | B-A Delivery | A-B Induction | B-A Induction | A-B Post Shock Pace | B-A Post Shock Pace |
|---|---|---|---|---|---|---|
| 88 | Closed | Closed | Closed | Closed | Closed | Closed |
| 80 | Closed | Open | Closed | Open | Closed | Open |
| 84 | Open | Closed | Open | Closed | Open | Closed |
| 82 | Open | Closed | Open | Open | Open | Open |
| 86 | Closed | Open | Open | Open | Open | Open |
| 76 | Open | Open | Open | Closed | Open | Closed |
| 78 | Open | Open | Closed | Open | Closed | Open |

Control circuit 60 controls the delivery of stimulation pulses to patient 12 coupled to the output circuit 72 by one or more electrodes 32, 34, or the housing electrode. In the exemplary schematic diagram shown in FIG. 5, the output circuit 72 includes H-bridge circuit 104, terminals HV-A and HV-B, and opt-in circuits 76, 78. The control circuit 60 controls the charging circuit 64 (FIG. 4) to generate the input signal for a stimulation pulse, e.g., pacing, defibrillation, or threshold testing, to patient 12 based on a selected one or more programs, which may be stored in memory. For example, control circuit 60 provides control output signals for control of the switches of the H-bridge 104. Further, for example, control circuit 60 controls the generation of arbitrary input signals for generation of the stimulation pulses. As such, the control circuit 60, alone or in conjunction with other circuit components such as the charging circuit 64 and a power source (not shown in FIG. 5), may function as a stimulation pulse generator. Such components may correspond to conventionally known stimulation pulse generators such as that described in U.S. Pat. No. 8,340,762, issued to Vonk et al and incorporated herein by reference in its entirety.

The H-bridge circuit 104 is connected between a high side 106 and a low side 108. The H-bridge circuit 104 includes first and second legs 110, 112 connected between the high side 106 and low side 108 thereof. The first leg 110 of the H-bridge circuit 104 includes first and second switches 80, 82 and the second leg 112 of the H-bridge circuit 104 includes third and fourth switches 84, 86. The first switch element 80 is connected towards the high side 106 and the second switch element 82 is connected towards the low side 108. Further, the third switch element 84 is connected towards the high side 106 and the fourth switch element 86 is connected towards the low side 108.

The opt-in circuit 76 is connected to the first leg 110 while the opt-in circuit 78 is connected to the second leg 112. Opt-in circuit 76 may include a resistor 120 that is connected in series with a power semiconductor device 122, such for example, as the transistors discussed above. Opt-in circuit 78 may include a resistor 124 connected in series with a power semiconductor device 126, such for example, as the transistors discussed above. The opt-in circuit 76 is connected in parallel with the switch element 82 while the opt-in circuit 78 is connected in parallel with the switch element 86. In the example implementation illustrated in FIG. 5, the drain of the power semiconductor device 122 is connected at the node between the switches 80 and 82 while the source is connected to the low side 108 through resistor 120. Similarly, the drain of the power semiconductor device 126 is connected at the node between the switches 84 and 86 while the source is connected to the low side 108 through resistor 124.

Each of the switches 80-84 may be implemented having substantially identical switch components. In one or more embodiments, any switch configuration may be used. However, the disclosure herein is not limited by this particular configuration and non-identical switches may be utilized in one or more different embodiments. The commands/operations for issuing control signals to control the opening and closing of the switches 80-86 may correspond to any techniques known in the art, such as software/firmware implementations, and will not be discussed in detail for the ease of description. Furthermore, one will recognize that, although FETs are used and described herein, one or more functions provided by such FETs may be implemented using other types of transistor devices (e.g., IGBTs) and that the present description is not limited to only the use of FETs or MOSFETs.

A patient 12 is connectable to the first leg 110 of the H-bridge circuit 104 at a node located between the first and second switches 80, 82 (e.g., first node HV-A) and to the second leg 112 of the H-bridge circuit 104 at a node located between the third and fourth switches 84, 86 (e.g., second node HV-B).

In operation, the output circuit 72 will utilize a plurality of configurations of the output circuit 72 to provide various functions of SIMD 14. For example, the switches 80-86 may be configured in a first configuration selected from a plurality of configurations to deliver a pacing therapy. In a further example, a second configuration selected from a plurality of configurations may be utilized to deliver a defibrillation therapy. In another example, a third configuration selected from a plurality of configurations may be utilized to deliver a stimulation pulse for performing a threshold testing to optimize a given therapy such as a defibrillation therapy. In yet another example, the switches 80-86 may be manipulated for removal of the DC polarization. That is, an initial pulse for a delivered therapy may be a negative polarity pulse discharged through first and second selected switches of H-bridge circuit 104, and thereafter, the DC polarization of the tissue electrode interface is removed by applying a pulse through third and fourth switches of H-bridge circuit 104.

Each of the plurality of configurations is implemented based on the biasing of the individual switches 80-86. The biasing of the switches 80-86 is performed under control of control circuit 60, which issues control signals to open and close the switches based on a predetermined program that may be stored in memory of the control circuit 60.

Control circuit 60 issues control signals that cause the output circuit 72 to be configured in one of a plurality of configurations, each of which is selected to provide one or more functions of the SIMD 14. In accordance with one embodiment of this disclosure, one of those functions is performing threshold testing to determine optimum stimulation parameters for delivery of therapy, such as pacing or defibrillation.

Although threshold testing has been described in conjunction with conventional implantable medical devices, the inventors have discovered that providing these waveforms using conventional techniques in a subcutaneous implantable device, such as SIMD 14, poses various challenges. Among those conventional techniques are solutions that utilize the full H-bridge for the threshold testing, thereby requiring components that increase the complexity and current consumption of the circuitry. Moreover, utilizing the conventional techniques in the subcutaneous implantable devices requires higher energies and durations for inducing the arrhythmia, relative to the transvenous implantable devices.

In accordance with one or more embodiments of the present disclosure, the threshold testing includes delivery of stimulation pulses to induce an arrhythmia in patient 12. The threshold testing may be performed during portions of operation of the SIMD 14 when therapy is not being provided. Accordingly, the present disclosure provides output circuit 72 that includes the H-bridge 104 and opt-in circuits 76 and 78. The output circuit 72 is selectively configured to provide the various functions of SIMD 14 such as delivery of stimulation pulses and/or sensing. In one or more configurations, the output circuit 72 is operated in a predefined configuration to deliver stimulation pulses for threshold testing to maximize the efficiency of the therapy delivery.

In operation, the output circuit 72 is configured to utilize one switch element on a first half of the H-bridge circuit 104 to select the appropriate positive electrode for the phase of the delivered waveform and one of the power semiconductor devices of the opt-in circuits 76, 78 is used to select the negative electrode thereby bypassing the second half of the H-bridge circuit 104. In this configuration, the combination of the series connected resistor and power semiconductor device of the selected one of the opt-in circuits 76, 78 provides current regulation for an induction waveform that is delivered to induce an arrhythmia in patient 12.

In an exemplary embodiment, the threshold testing may be performed by delivering a stimulation pulse in the form of a relatively low energy shock (commonly referred to as a T-shock) or one or more stimulation pulses to the cardiac tissue of patient 12 during the vulnerable period of the cardiac cycle. The one or more stimulation pulses may have a frequency about 10 Hz to about 100 Hz, and preferably with a frequency of about 25 Hz to about 85 Hz, and more preferably with a frequency of about 40 Hz to about 70 Hz, and even more preferably with a frequency of about 50 Hz to about 60 Hz, and most preferably with a frequency of about 50 Hz. The techniques for identifying the vulnerable period of the cardiac cycle are known and include that described in U.S. Pat. No. 8,064,996, issued to Belk et al and incorporated herein by reference in its entirety. The output circuit 72 is configured in one of several configurations to deliver the stimulation pulse(s) for the threshold testing at a period that is synchronized or concurrent or coincident with the identified vulnerable period of the cardiac cycle. The at least one stimulation pulse is generated from the energy stored in the energy storage capacitors 62 that are charged to a selected energy level.

In a first configuration, the opt-in circuit 78 may be used in conjunction with switch 88 and switch 80 of the H-bridge circuit 104 for the threshold testing. The switches 88 and 80 are biased in a conducting state in order to provide a path from the capacitors 62 to electrodes 32, 34 for the application of a first phase of a stimulation pulse to the patient 12. The stored energy travels from the positive terminal of the capacitors 62, through switches 88 and 80, across the patient 12, and back through opt-in circuit 78 to the negative terminal of the capacitors 62.

In this first configuration, the return current path defined through opt-in circuit 78 to the negative terminal on the lead 18 completes the conduction path for the induction stimulation pulse delivered to the patient 12 across the electrodes. The control circuit 60 issues a control signal to cause the power semiconductor device 126 to work in conjunction with the series-connected resistor 124 to provide current regulation for the induction waveform. The control signal issued by control circuit 60 causes the semiconductor device 126 to be operated in the linear region (also known as triode mode/ohmic mode). For example, in the case of a semiconductor device 126 implemented as a MOSFET transistor, the MOSFET will operate like a resistor, due to the control signal being configured to control the gate voltage relative to both the source and drain voltages. Switches 82, 84, and 86 are biased in a non-conducting state during the first phase. As such, the lower half of the H-bridge is bypassed in this first phase.

In another configuration, the opt-in circuit 76 may be used in conjunction with switch 88 and switch 84 of the H-bridge circuit 104 for the threshold testing. The opt-in circuit 76 and switches 88, 84 may be biased in a conducting state for a second phase of the stimulation pulse. As such, the delivery path extends from the positive terminal of the capacitors 62, through switches 88 and 84, across the electrodes 34, 32 coupled to the patient 12, with the path being completed at the negative terminal of the capacitors 62 via opt-in circuit 76. The polarity of the second phase of the stimulation pulse is therefore opposite in polarity to the stimulation pulse delivered in the first phase.

In this configuration, the control circuit 60 issues signals to control operation of the semiconductor device 122 in the triode mode as described above. As such, the series-coupled semiconductor device 122 and resistor 120 will function to provide current regulation as described above with reference to semiconductor device 126 and resistor 124.

Alternative embodiments may provide for delivery of biphasic stimulation pulses. In such embodiments, the output circuit 72 may be configured to deliver a first phase of a stimulation pulse having a first polarity by using one of the opt-in circuits 78, 76 (in conjunction with the corresponding switch 80, 84 as described above), followed by delivery of a second phase of a stimulation pulse having a second polarity by using the other of the opt-in circuits 76, 78 (in conjunction with the corresponding switch 84, 80 as described above).

In accordance with some embodiments of the present disclosure, the H-Bridge circuit 104 is configured such that only two switches of the H-Bridge 104 (e.g., 80 and 84) are utilized in conjunction with the opt-in circuits 76, 78 for bi-phasic delivery of a stimulation pulse for threshold testing. In other embodiments, a pair of opt-in circuits (not shown) may be coupled in a similar manner as circuits 76, 78 to the switches 82 and 86 for bi-phasic delivery of a stimulation pulse for threshold testing. In embodiments where monophasic delivery is desired, then only one of the switches is utilized. Utilizing one of the opt-in circuits 76, 78 in the delivery of the threshold testing stimulation pulse to bypass the switches that is coupled in parallel with the selected opt-in circuit enables current regulation of the stimulation pulse that facilitates a reduction in the duration and/or energy levels required to generate an effective stimulation pulse. Nevertheless, having all four switches 80-86 allows a plurality of functions of the SIMD 14 to be performed, such as, therapy (pacing or defibrillation) stimulation pulse delivery and removal of the DC polarization.

Figure 6:
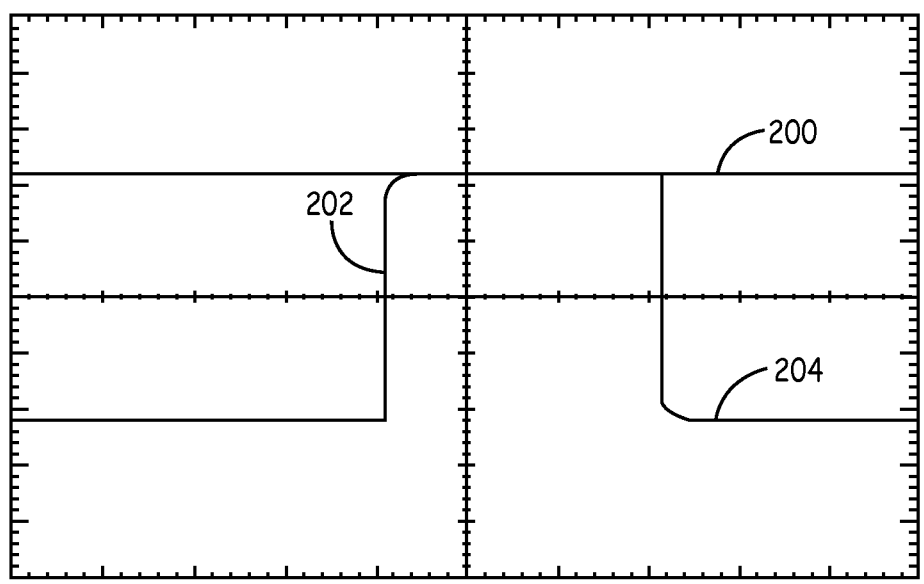
FIG. 6 is a diagram illustrating arbitrary input signals and resulting delivered waveforms using, for example, the output circuit that is schematically shown in FIG. 5.

FIG. 6 is a diagram illustrating arbitrary input signals (e.g., selected input waveforms) and the resulting waveforms that are delivered using, for example, output circuit 72, such as schematically shown in FIG. 5. As used herein, the term "arbitrary" input signal refers to the ability to select any shape of input (e.g., voltage waveform, static DC level input, shaped waveform, etc.) for use in generating a resulting current waveform (e.g., that generally follows the same shape (e.g., a ramped voltage input waveform being used to generate a ramped delivered current waveform, a static input used to deliver a proportional current, etc.)).

A static input signal (e.g., a 1.5 V static input) delivered by capacitors 62 may be utilized to generate a proportional delivered waveform (e.g., measured across a 500 ohm load). For example, when the output circuit 72 is operational and a static input waveform 200 is applied, with the switches 80 and 86 being selected, a stimulus pulse or delivered waveform 202 having a first polarity (e.g., a positive polarity) is applied to the patient 12. Further, for example, when the output circuit 72 is operational with the static input waveform 200 being applied, and the switches 82 and 84 are selected, a stimulus pulse or delivered waveform 204 having a second polarity (e.g., a negative polarity) is applied to the patient 12.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. An implantable cardiac stimulation device, comprising:
a stimulation pulse generator operable to generate stimulation pulses in accordance with a treatment regimen;
at least two electrodes; and
an output circuit coupled to the stimulation pulse generator and operable to deliver the generated stimulation pulses through the at least two electrodes, the output circuit including:
a H-bridge having a high side and a low side, and a first opt-in circuit electrically coupled to the H-bridge wherein, the output circuit is selectively configured in a first configuration to deliver a therapy stimulation pulse through the high side and the low side, and in a second configuration to deliver an arrhythmia induction stimulation pulse through the high side and the first opt-in circuit, wherein the first opt-in circuit is electrically coupled to the low side of the H-bridge in a parallel arrangement such that the arrhythmia induction stimulation pulse bypasses the low side responsive to the output circuit being configured in the second configuration.

2. The implantable cardiac stimulation device of claim 1, wherein:
the H-bridge includes a high node, a first node, a second node, and a low node,
the high side of the H-bridge includes a first switch coupled between the high node and the first node and a second switch coupled between the high node and the second node,
the low side of the H-bridge includes a third switch coupled between the first node and the low node and a fourth switch coupled between the second node and the low node,
the first opt-in circuit is coupled between the first node and the low node in parallel with the third switch,
a first electrode of the at least two electrodes is coupled to the first node, and
a second electrode of the at least two electrodes is coupled to the second node.

3. The implantable cardiac stimulation device of claim 2, further comprising a second opt-in circuit coupled between the second node and the low node in parallel with the fourth switch.

4. The implantable cardiac stimulation device of claim 1, wherein the first opt-in circuit comprises a current regulator having a resistor coupled in series to a transistor.

5. The implantable cardiac stimulation device of claim 4, further comprising a control circuit to control the transistor to operate in a triode mode during the second configuration to cause such that the current flow through the first opt-in circuit.

6. The implantable cardiac stimulation device of claim 1, wherein the stimulation pulse generator comprises a power source, an energy storage capacitor, and a control circuit configured to control the charging of the energy storage capacitor by the power source and the timing of the generation of the stimulation pulses for delivery of the therapy stimulation pulse and arrhythmia induction stimulation pulse.

7. The implantable cardiac stimulation device of claim 1, wherein the arrhythmia induction stimulation pulse is delivered to coincide with the vulnerable period of a cardiac cycle.

8. The implantable cardiac stimulation device of claim 1, further comprising a control circuit for dynamically configuring the output circuit in one of the first and second configurations.

9. The implantable cardiac stimulation system of claim 1, further comprising a cardiac electrical sensor operable to sense cardiac electrical signals between the at least two electrodes, wherein:
a T-wave of the cardiac signal is identified in response to the sensed cardiac electrical signals, and
the arrhythmia induction stimulation pulse is delivered coincident with the identified T-wave.

* * * * *